United States Patent [19]

Garcia

[11] Patent Number: 5,065,315

[45] Date of Patent: Nov. 12, 1991

[54] SYSTEM AND METHOD FOR SCHEDULING AND REPORTING PATIENT RELATED SERVICES INCLUDING PRIORITIZING SERVICES

[76] Inventor: Angela M. Garcia, 21753 Town Place Dr., Boca Raton, Fla. 33433

[21] Appl. No.: 426,113

[22] Filed: Oct. 24, 1989

[51] Int. Cl.$^5$ ............................................. G06F 15/42
[52] U.S. Cl. ............................... 364/413.01; 340/721; 364/413.02
[58] Field of Search .... 364/413.01, 102, 200 MS File, 364/922, 919, 244.5, 222.2; 340/717, 720–721, 723; 235/380

[56] References Cited

U.S. PATENT DOCUMENTS

| | | | |
|---|---|---|---|
| 3,872,448 | 3/1975 | Mitchell, Jr. | 364/200 |
| 4,835,372 | 5/1989 | Combrich | 235/462 |
| 4,857,713 | 8/1989 | Brown | 364/401 |
| 4,916,441 | 4/1990 | Gombrich | 235/380 |

OTHER PUBLICATIONS

Brimm, John E., "Computers in Critical Care", Critical Care Nursing Quarterly, Mar. 1987.
"Ulticare: A Bedside Patient Care Information System", Brochure from Health Data Sciences Corp.
"78707A POMS Clinical User's Guide", Brochure by Hewlett Packard, Jan. 1982.
"Better Care, Shorter Stays Thanks to Networking", Data Communications, Nov. 1986, Principi et al.

*Primary Examiner*—Gail O. Hayes
*Attorney, Agent, or Firm*—Harry W. Barron

[57] ABSTRACT

A hospital computerized system includes a terminal in all departments of the hospital for entering information pertinent to a patient's stay in the hospital. The initial information entered, as a part of the admitting procedure, includes the patient's history and admitting physician's physical examination results. It additonally includes the physician's orders for tests or hospital services to be performed. The system prints a history and physical report for the patient's chart and highlights the abnormal findings and complaints. The system additionally schedules all hospital services for the patient, thereby eliminating this responsibility from the nurses and other hospital personnel, and avoids situations where the patient is scheduled to be in two places at the same time. The scheduling system is capable of rescheduling tests or services in cases of emergencies. Test results and/or technicians's comments are entered into the system through terminals in each department and the results and comments are printed at the nurses' station for inclusion in the patient's chart. Additionally, physician's and nurses' notes and findings are entered into the systems and printed at the nurses' station for inclusion in the chart. The system finally prints a discharge planning document and a narrative discharge report for the chart, as well as a patient instruction document. The information entered into the system may be used by the billing program to bill the patient for all services and tests performed.

18 Claims, 3 Drawing Sheets

| 1 | INDENTIFICATION |
| --- | --- |
| | NAME etc _____ |

| 2 | CHIEF COMPLAINT |
| --- | --- |
| | _____ |
| | _____ |

| 3 | PRESENT ILLNESS |
| --- | --- |
| | _____ |
| | _____ |

4 REVIEW OF SYSTEMS

| GENERAL 32 | SKIN | | THROAT |
| --- | --- | --- | --- |
| ☐ WEAKNESS | ☐ COLOR CHANGE | | ☐ SORENESS |
| ☐ FATIGUE | ☐ NAIL CHANGE | | ☐ BAD TONSILS |
| ☒ FEVER | ☐ HAIR CHANGE | | ☐ HOARSENESS |
| ☒ CHILLS | ☐ MOLES | | ☐ PAIN |
| ☒ NIGHT SWEATS | ☐ RASHES | | ☐ TROUBLE SWALLOWING |
| ☐ FAINTING | ☐ ITCHING | | ☐ RECURRENT INFECTIONS |

| 5 | PAST MEDICAL HISTORY |
| --- | --- |

| 6 | FAMILY HISTORY |
| --- | --- |

| 7 | SOCIAL HISTORY |
| --- | --- |

FIG. 2.

Figure 3:
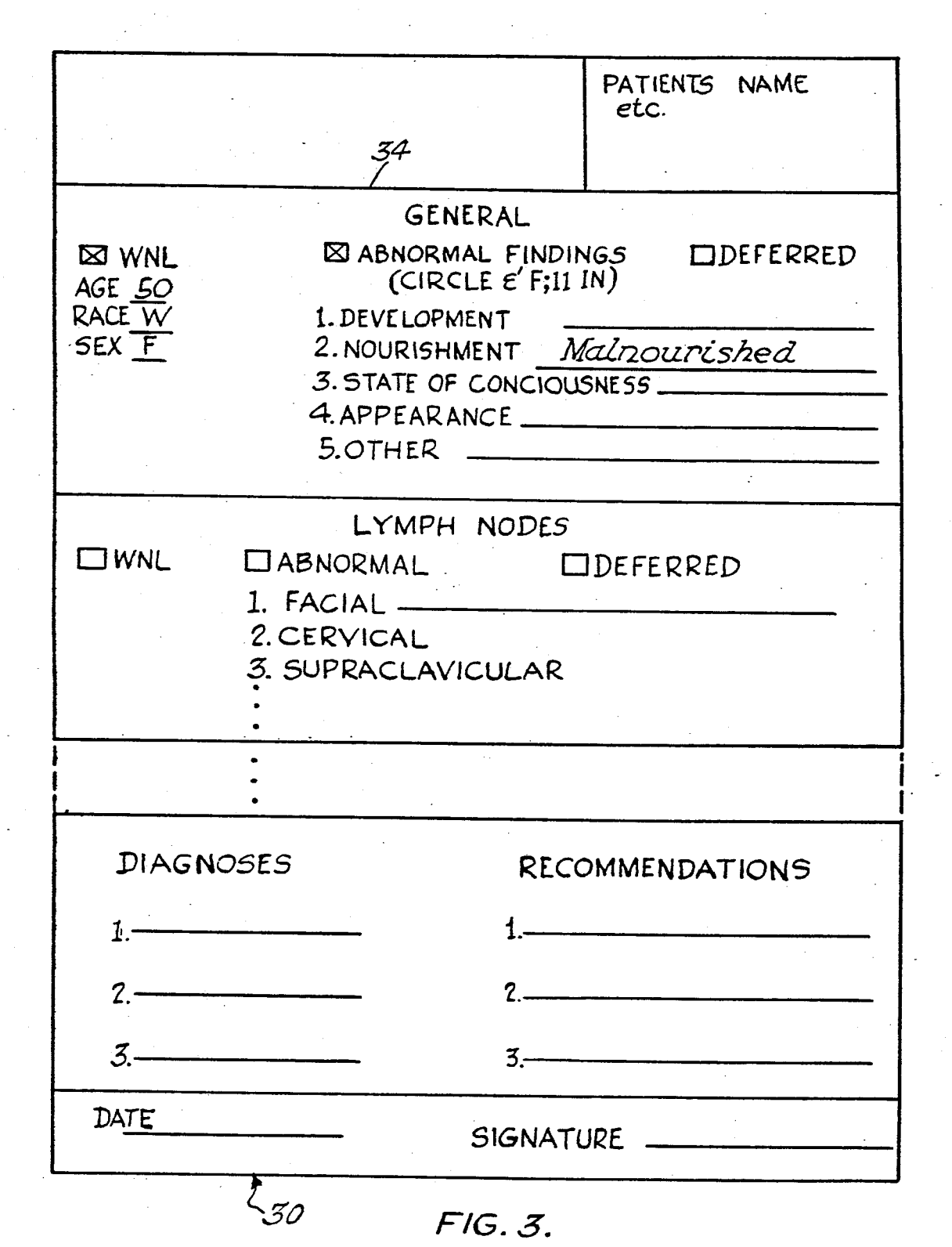

|  | PATIENTS NAME etc. |
|---|---|
| 34 | |

GENERAL

☒ WNL     ☒ ABNORMAL FINDINGS     ☐ DEFERRED
(CIRCLE e' F;11 IN)

AGE 50
RACE W
SEX F

1. DEVELOPMENT _____
2. NOURISHMENT  *Malnourished*
3. STATE OF CONCIOUSNESS _____
4. APPEARANCE _____
5. OTHER _____

LYMPH NODES

☐ WNL     ☐ ABNORMAL     ☐ DEFERRED

1. FACIAL _____
2. CERVICAL
3. SUPRACLAVICULAR

⋮

| DIAGNOSES | RECOMMENDATIONS |
|---|---|
| 1. _____ | 1. _____ |
| 2. _____ | 2. _____ |
| 3. _____ | 3. _____ |

DATE _____     SIGNATURE _____

SYSTEM AND METHOD FOR SCHEDULING AND REPORTING PATIENT RELATED SERVICES INCLUDING PRIORITIZING SERVICES

This invention relates to a hospital medical record maintenance, generation and scheduling system, and more particularly, to a computerized system located throughout the hospital facility for maintaining and generating required medical records for a hospitalized patient and for scheduling various tests, therapies and other hospital services for that patient.

In the past, record keeping for a hospitalized patient has been a major problem for the proper administration of a hospital and a major administrative drain on the time of the medical staff. A patient's chart, or file, is typically maintained at the nurse's station, which is in the area of the patient's hospital room. However, documents from various parts of the hospital, such as laboratory reports, physical therapist's reports, doctor's reports and the like are continually generated at locations throughout the hospital, or in other places remote from the hospital, and must be placed in this chart. The need for continual access to the chart places additional work on the hospital support staff, such as the nurses and technicians, who must either travel to the chart area, or telephone the nurses station for a report on information contained in the chart. Further, a substantial expenditure of money on the part of the hospital results because of the necessity of employing runners or messengers to physically carry the various reports to the nurses station for inclusion with the chart. These procedures can delay the placing of important documents in the patient's chart for review by physicians and nurses.

Another problem commonly present in most hospital systems is the scheduling of patients for various services performed by the hospital. Some services, such as physical therapy, respiratory therapy, X-rays and the like may only be able to handle one, or a few, patients at a time. Further, a patient can only be scheduled to be in one place at a time. In order to properly schedule patients, the technicians in the various service organizations and nurses on the patient floor are constantly communicating by telephone to set up appropriate schedules. This takes up valuable time of the hospital personnel, which otherwise could be used for direct patient care. Furthermore, emergency situations often occur in a hospital, resulting in changes to the schedule to permit the emergency tests to be performed, thereby causing normally scheduled non-emergency tests to either be rescheduled or causing the patient to wait for long periods of time at the service area. Again, this takes up additional time of the hospital support staff which could better be utilized in providing direct patient care.

In addition to the above, there are many other problems which reduce the time that scarce medical staff has available to provided direct patient care. For example, for every patient discharged from a hospital, a discharge summary must be prepared based on the patients hospital stay. Much of the information contained in the discharge summary is contained in the patient's chart and needs to be summarized or abstracted before being placed in the discharge summary. In addition, physicians must dictate the discharge summary relating to the medical conclusions and future care of the patient. This results in additional physician time and inherent delays in the preparation of the discharge summary, since, after being dictated by the physician, it must first be sent to a transcription service firm, which typically is at a location remote from the hospital, and then returned to the hospital for inclusion with the chart before the patient is discharged. A similar problem exists for the history and physical reports, which are generated at the time the patient is admitted.

Most hospitals possess computer systems which are used for much of the administration within the hospital. For example, in most hospitals, computer systems provide the bills for the patients. To generate a bill, substantial data, such as tests and services performed, must be entered into the computer in order for the bill to be generated. Because of the existence of computerized billing utilized in most hospitals, computer terminals are typically positioned throughout the hospital in order to permit the data to be entered at the location that the charge is generated. For example, when laboratory tests are performed, the data is entered into the billing computer directly from the laboratory are so that the cost of the test can be placed on the patient's bill. However, much of the same data may be hand carried to the patient's chart for review by the medical staff.

One could substantially increase the efficiency and reduce the paper work in a modern hospital by more fully utilizing existing computer systems, or by installing supplemental systems, to relieve much of the administrative burdens placed on physicians and support staffs in the hospitals. For example, the maintenance of medical records can be substantially simplified by utilizing computer technology. In addition, the scheduling of patients can be simplified using the computer technology. By combining functions, such as scheduling and chart report generation into single systems, considerable efficiencies and duplications are further eliminated. Since much of the information is already being entered into a computer system for billing purposes, the incremental additional work is minimized. For example, one must now type in the various laboratory tests performed for billing; to additionally type in the test results would not require significant additional effort. The benefit, of course, is that once the test results are entered into the system, anyone with access to a terminal and a password can see the results without physically going to the chart or without calling and disturbing a nurse. Further, as soon as the results are typed into the system, they can be printed at the nurses' station and immediately be placed in the patient's chart.

The prior art discloses various computer systems which control portions of a hospital system, but nothing shows the entire integrated system as proposed herein. For example, reference is made to the following U.S. patents which show various prior art hospital computerized systems: U.S. Pat. No. 3,872,448 in the name of Baker A. Mitchell, Jr. and entitled, "Hospital Data Processing System"; U.S. Pat. No. 4,135,241 in the name of Eugene A. Stanis et al and entitled, "Inventory Control, Bed Allocation and Accounting Data Handling System"; U.S. Pat. No. 4,315,309 in the name of Robert D. Coli and entitled, "Integrated Medical Test Data Storage and Retrieval System"; U.S. Pat. No. 4,491,725 in the name of Lawrence E. Pritchard and entitled, "Medical Insurance Verification and Processing System"; U.S. Pat. No. 4,591,974 in the name of Donald H. Dornbush et al and entitled, "Information Recording And Retrieval System"; U.S. Pat. No. 4,658,357 in the name of Gary T. Carroll et al and entitled, "Time and Accounting System"; and U.S. Pat. No.

4,817,050 in the name of Kenichi Komatsu et al and entitled, "Database System".

In accordance with one aspect of this invention, there is provided a scheduling and reporting system for hospital patients comprising means for entering location data regarding each patient and physician orders for hospital services to be performed for each patient. Further, the system includes means for scheduling the ordered services for each patient and for reporting the schedule information to a common area in the vicinity of each patient's location. The system further includes means for recording and reporting the results of the services administered to each patient to the common area in the vicinity of each patient's location. Finally, the system includes means responsive to the recorded information for generating a discharge summary report for each patient at the conclusion of the hospitalization of such patient.

In accordance with another aspect of this invention, there is provided a method of scheduling patient services and recording patient data for a hospitalized patient comprises the steps of recording and location for each patient and recording physician orders for services to be performed upon each patient. Additionally, the method includes the steps of automatically scheduling the services for each patient, recording the results of the performance of such services and providing the discharge summary record for each patient.

One preferred embodiment of the subject invention is hereafter described with specific reference being made to the following figure, in which:

FIG. 2 illustrates a form a patient may use to provide medical history information for entrance into the computer system of the subject information; and FIG. 3 illustrates a form a physician may use in providing information relating to a physical examination for entrance into the computer system of the subject information.

Figure 1:
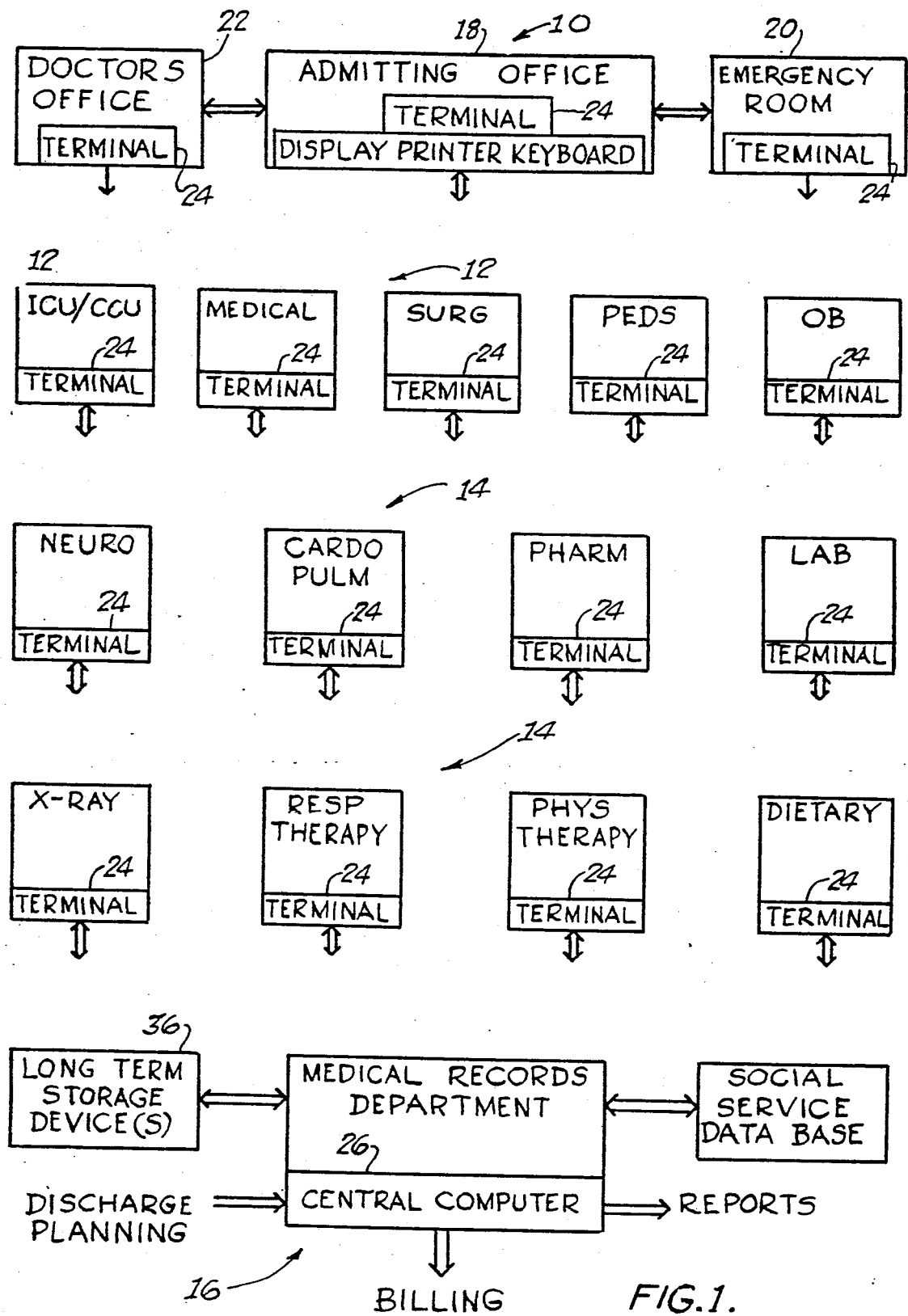
FIG. 1 shows a block diagram of the improved medical records and scheduling computer system.

Referring now to FIG. 1, a diagram illustrating the various areas of a hospital which would use the subject invention is shown. These various areas include the admitting area 10, the nurses' stations 12, the various hospital service departments 14 and the medical record's department 16. Within each of these areas 10, 12, 14 and 16, many sub-areas, to be specified hereafter, are included. Typically, each individual area or sub-area of a hospital operates independent of other areas or sub-areas; however, each area or sub-area must constantly communicate with certain other areas or sub-areas to make information generally available. One purpose of the present invention is to facilitate orderly, efficient and rapid communication among the various areas of the hospital and to provide such information with minimal human intervention between the various areas and sub-areas, as necessary.

Referring specifically to the admitting area 10, the one portion of the hospital that every patient associates is the admitting office 18. A patient may be admitted to a hospital, through admitting office 18, either through the emergency room 20 or by direct admittance from a doctor's office 22. Normally, some sort of a medical history, physical examination results and physician orders are sent to admitting office 18 by the admitting physician. At the admitting office, a patient's chart is initially set-up and the patient is assigned to a particular bed location in the hospital. Reports of the initial physical examination and patient history, as well as the physician's orders are then placed in the chart. Other documents, such as prior hospital discharge reports may also be placed in the chart.

When using the subject invention, the bed location and other pertinent patient data (name, address, age, sex, etc.) of the patient and the physician admitting orders and history and physical information are entered into terminal 24. This information is transmitted to and stored in main computer 26 in the medical records department 16 and may be accessed by any of the other terminals 24 shown in FIG. 1. Of course, the information may be subject to password or other security procedures, which procedures are well known in the art.

The history and physical information may be derived from an emergency room physician's examination of a patient brought into emergency room 20 and may be entered from the terminal 24 in either the admitting office or the emergency room 20. Alternatively, the history and physical information may have been generated earlier during an examination at doctor's office 22 and may be entered from a terminal 24 contained in the doctor's office 22 directly to the admitting office and to computer 26. In such case, the patient may be pre-admitted and go directly to an assigned room without visiting the admitting office 18, or with only a short visit to the admitting office 18.

One time saving technique for entering the history and physical information utilizes a program in which all normal components of a patient's history and physical examination are preprogrammed. Such a program permits the physician to merely recite abnormal findings by dictating or checking a form for later data entry of the abnormalities. A form 28, of a type which may be completed by the patient, with or without assistance from a nurse or other member of the physician's staff, is shown in FIG. 2. A form 30, of a type which may be used by the physician for providing the information results of a physical examination, is shown in FIG. 3. Alternatively, the physician may use form 30, shown in FIG. 3, as a guide in dictating a physical examination report and need only dictate the abnormal findings. As seen in both FIGS. 2 and 3, both forms 28 and 30 list many possible problems which could be associated with a particular patient. To use the forms 28 and 30, only the abnormal blocks need be checked. When the data is entered into the terminal 24, the screen prompting the data entry operator will be organized similar to the various sections of the forms 28 and 30 and the information on the forms 28 and 30 is thereby easily entered through terminal 24 into computer 26 of the system shown in FIG. 1. An example of the entire forms 28 and 30 is shown in Appendix I and Appendix II hereto, respectively.

As seen in FIG. 2, the patient history portion of the required information is initially provided by the patient filling in the lines or checking the appropriate blocks of form 28. The blocks are organized by the various medical systems of the body. As seen from FIG. 3, the physical examination form 30, as well as the program of computer 26, segregate each various part of the body, so that a physician may indicating by a checkmark or by dictation, that a particular part of the body has no medical problems. This is indicated by the WNL (within normal limits) block. Alternatively, where particular medical problems are found during the physical examination, that problem is manifested by either circling a system, followed by a comment to be filled in the blank on the form. Alternatively, the physician may dictate the abnormal results of the examination by simply referring to form 30 as a guide. Form 30 further includes a block labeled "DEFERRED" which may be checked if no examination of that particular body system was made, or if a referral to another physician is necessary.

From the information provided using the forms 28 and 30 in FIGS. 2 and 3, a history and physical report meeting the requirements of the Joint Commission For Accreditation Of Healthcare Organizations can be prepared by computer 26, setting forth the entire physical condition of the patient including both normals and abnormalities. The output device, such as the printer or screen monitor, or both, is programmed to print or display the abnormalities in bold, underlined or italics text for easy scanning by other physicians and medical service personnel. The history and physical report includes both the patient's past medical history, which is typically generated by the patient, and the results of a physical examination. In either case, it is necessary to only enter the abnormalities because the normals are pre-programmed within the system.

Where a patient has completed the General section 32 of form 28 shown in FIG. 2 by checking the Fever, Chills and Night Sweats blocks under the General system block 32, the history and physical report may include a clause under the heading Clinical History, as follows: "General: The patient complains of fever, chills and night sweats. The patient reports no weakness, fatigue nor fainting." The report may contain the following sentence under the heading Physical Examination, where the physician has checked, or dictated, for the General block 34 as seen in FIG. 3, that the patient is a 50 year old White Female, that is malnourished. "General: The general examination reveals this 50 year old white female is well developed, is malnourished, alert, does not appear acutely ill and is cooperative." It should be noted that in the narrative transcript report, the portions checked or completed are printed in a bold print and the items left blank are printed in normal print. This makes a review of the report easier for those wishing to scan for only medical problems.

Once the patient has been admitted through admitting office 18 and the chart has been prepared, the physician's order document and the history and physical examination report are inserted into the chart. Then, both the patient and chart are transferred to the assigned bed location. If the patient had previously been hospitalized and the subject system had been in use, the past discharge summary could also be retrieved from long term storage device 36 and reprinted for inclusion in the chart. This will be described in more detail hereafter.

Every bed location in a hospital is in a defined type of patient areas, typically a floor, wing, etc. For example, typical floors, wings, or patient areas of a hospital include the ICU/CCU area for critically ill patients, the medical area for patients undergoing diagnostic testing or recovering from illnesses, the surgical area for pre-operative and post-operative patients, the pediatrics area for children and the obstetrics area for obstetric's patients. Of course, different hospitals may have different or additional patient areas. Within each of the various patient areas of a hospital, a central nurses' station is typically present and such nurses' stations are shown in FIG. 1 in nurses' station block 12. Located at each of the nurses' stations 12 is a terminal 24, which includes a keyboard, screen display and printer device.

When the patient is transferred to the bed in one of the nurses' station 12 areas of the hospital, the chart is physically stored at the central nurses station. New documents are to be placed into the chart as they are received on the printer associated with terminal 24 at the particular nurses' station. In addition, nurse's initial assessments, patient readings, such as blood pressure, temperature, fluid intake and output etc., and other similar information may be entered and printed through the nurse's station terminal 24. This permits the information to be stored in the central computer 26 and exist in the patient's chart. In addition, the information that is entered through one of the terminals 24 is stored in central computer 26, as well as being printed on the printer at the nurses' station for inclusion in the paper chart. As will be discussed hereafter, the information printed on the nurses' station printer may also be entered at various other locations in the hospital.

At the time the physician's orders were entered in admitting office 10, the information was stored in central computer 26. Typical of the physician's orders would be the performance of certain tests, such as laboratory tests, X-rays, neurology tests and the like, and the provision of certain therapies for the patient, such as physical therapy, respiratory therapy and the like. Additionally, the physician may order certain medication for the patient from the hospital pharmacy or special diets for the patient from the hospital dietary department. The information entered from the physician order is stored in computer 26 and transferred to the appropriate hospital service departments 14, where it is printed or displayed on the terminal 24 at such department. As an example, the various departments in a hospital may be the Neurological (NEURO) department, the Cardio-Pulmonary (CARDIO PULM.) department, the pharmacy (PHARM) department, the Laboratory (LAB) department, the Radiology (X-RAY) department, the Respiratory Therapy (RESP. THERAPY) department, the Physical Therapy (PHYS. THERAPY) department, and the kitchen (DIETARY) department.

For the hospital departments 14 giving tests or providing therapy services, it is not sufficient to merely advise each of the departments 14 of the fact a test is to be performed or that a certain therapy is to be given. Many tests or therapies are available to one, or a limited number of patients at a time. Further, a patient can only be at one place at any given time. For example, certain X-ray tests are only available for one patient at a time and it is necessary to schedule the patients to fully utilize the X-ray equipment, while at the same time not delaying for unacceptably long periods the time required to perform the X-ray. Thus, it is desirable that computer 26 schedule the time each test and therapy is to occur for the entire hospital.

At the time the physician order is entered through terminal 24 at the admitting office 18, the tests requested may be designated in a priority manner. For example, the physician may determine that the test should be performed STAT, indicating immediately, ASAP (as soon as possible), indicating that same day, or Routine, indicating during the next available time slot. Where a high priority test is ordered, computer 26 may have to reschedule previously scheduled tests. This is easily accomplished by a conventional scheduling program and by printing or displaying the rescheduled times at both the department terminal 24 and the nurses' station terminal 24. As the tests and therapies are completed, the schedule may be revised to minimize patient waiting where the department is behind schedule, or to minimize technician waiting if a department is ahead of schedule.

After tests are completed, the test result information is transmitted by the testing department to computer 26 and computer 26 causes the information to be printed on the printers at the appropriate nurses's station 12 closest to the patient's location. The test results may include raw test results, such as blood test results, or may include interpretations made by a physician, such as in the case of an X-ray or EKG reading. Again appropriate forms to be completed, or to serve as dictation guides, similar to forms 28 and 30 in FIGS. 2 and 3, may be used by the physicians interpreting the test results. Once the test results are printed at the nurses' station, the printed paper is placed in the patient's chart. Since the test results or interpretations are also stored in central computer 26, the attending physician, or a consulting physician, is able to review the results from their own terminal 24 without having to go to the hospital. When the test results are entered, computer 26 further causes appropriate billing for the tests performed. By using the same system that schedules and reports test results to derive billing information, duplicate billing and non-billing situations can be reduced.

In addition to utilizing the nurses station terminals 24 for displaying the scheduled information, the nurses initial histories and daily patient information, such as blood pressure, heart rate, temperature, respiratory rate and fluid intake and output can be recorded and stored in computer 26. Each of the patient information entries may be reported back to nurses station 24 or, as will be explained hereafter, printed in a discharge summary in the form of graphs or in an abstracted form as determined by the program for computer 26. In addition, the information may be printed at the nurses' station terminals 24 for inclusion in the patient's paper chart for referral by physicians or other medical personnel. Since the same information will be stored by computer 26, it may also be reviewed by a physician having access to a terminal in his office without having to come to the hospital.

Each of the various hospital service departments receive instructions and/or provide results or comments to terminals 24 associated in their area. Further, billing information is normally taken from the provision of the results or comments indicating that the ordered service has been completed. For some services, only test results are reported. For other services, comments of a therapist or physician are reported. In all instances, the reported information is stored in the memory of computer 26 and printed at the nurses' station for inclusion in the patient's chart. In addition, additional physician generated information may be entered from a terminal 24 and stored in computer 26, particularly where new patient ailments or a change in treatment occur. Also, medical findings may be entered and stored in computer 26.

The above described sequence of scheduling and data reporting continues for the duration of the patient's stay in the hospital. When the patient is to be discharged from the hospital, a discharge summary report must be prepared, which meets the requirements of the Joint Commission For Accreditation Of Healthcare Organizations. Portions of the discharge summary report include items dictated by the physician or entered by completing the Discharge Planning form attached hereto as Appendix III. In addition, other portions include a summary, or abstracting, of the test result data, the treatments, new complaints and the like.

In preparing the Discharge Summary report, computer 26 prepares the Discharge Planning document (Appendix III) for completion by the physician. The Discharge Planning document is based upon the initial patient complaints and abnormal findings entered at the admitting office 18, as supplemented by additional patient ailments and abnormal physical findings entered during the patient's stay in the hospital. The Discharge Planning document is generally requested by the attending physician the day prior to anticipated discharge and is completed so that the proper discharge documents may be prepared in time for the patient's discharge the next morning. The Discharge Planning document is in a form which first lists each diagnoses listed on the Physical Examination Report (FIG. 3 and Appendix II) entered as part of the admitting procedure, as supplemented by additional diagnoses made during the hospital stay and entered as physician's comments. Next, a section for a discharge diagnoses is provided for completion by the physician.

Thereafter, the Discharge Planning document lists the various patient complaints and includes an area for the physician completing the Discharge Planning document to check whether the complaint was stable, improved spontaneously, resolved spontaneously, improved with treatment or resolved with treatment. In addition, a block labeled "Other", together with an associated space, is provided. For complaints which changed, or were resolved, with treatment, a space is provided for physician's comments. Next a similar section is provided based upon the physical examination abnormal findings entered originally, or as supplemented during the hospitalization.

Finally, a summary and abstraction of the various department 14 reports is provided. These may include the admission, or first, reading, discharge, or last, reading and the hospital course reading. The hospital course reading is a reading between admission and discharge and may typically be the highest, or most abnormal reading. If all intrim readings were normal, the hospital course reading may be left blank. Of course, some services may not have been utilized during the hospitalization and will be blank, or there may only be one or two readings. In addition, a place is provided for the physician completing the Discharge Planning document to indicate that a particular section is non-contributory and should be left out of the discharge summary report.

The Discharge Planning document concludes with a prognosis section, a discharge instruction section and a disposition section, all of which are to be completed by the attending physician. The disposition section is used to indicate whether the patient is to be allowed to go home, to a nursing home, a rehab center, or the like. If the patient is to go to a nursing home, rehab center or the like, a social service module of the program of computer 18 includes a database for determining whether such a facility is available for that patient. If not, the final Discharge Report may be delayed. Alternatively, the disposition may indicate that the patient is referred to another physician, generally a specialist for the ailment determined during hospitalization.

Once the Discharge Planning Document is completed by the physician, a Discharge Summary document is prepared in narrative form, with the abnormal results highlighted, such as being printed in bold. In addition, Discharge Instructions in layman's terms are prepared and handed to the patient upon discharge. Of course, the patient's final bill is provided at the same time.

In case the patient ever returns to the hospital, it would be advantageous to be able to recall the significant events of the prior hospital stay. In order to provide this information, the discharge summary, and other pertinent information may be stored in a long term storage device 36, such as a laser disk memory. In such a system, multiple disks may be necessary and will be typically organized based upon a period of time. Each patient entry may be cataloged by patient name and/or social security number, for example, and a master database, sortable by patient name and/or social security number, should be maintained for the multiple disks, so that the next time the patient enters the hospital, the pertinent information may be retrieved, reprinted and placed in the patient's chart. At most, one disk per hospitalization will have to be loaded into storage device 36 and the patient's past hospitalization history can be quickly retrieved. In other words, it is no longer necessary to go to the warehouse and retrieve the paper chart from storage to see the pertinent events of the prior hospital stay.

From the above description, it is seen that the same information is used for many different aspects of the required records management requirements for patient care. Further, the computer system is programmed to abstract certain information and ignore other information based upon the normality or abnormality of the results, thereby making the task of the medical personnel easier and freeing time for patient care.

While the subject computerized hospital system has been described as a series of remote terminals 24 communicating with a central computer 26, the system may be set up as one or more local area networks, or a combination of such systems.

CLINICAL HISTORY Page 1

Admn. Date: _____  Admn. Time: _____
Admn. #: _____  Med Surg  Direct ER

1 IDENTIFICATION *this confidential history will be part of your permanent records.

Name _____ First _____ Middle _____ Sex: M F  Date of Birth _____
Physician _____ Social Security # _____ Date _____

2 CHIEF COMPLAINT State your main complaint. Example: Pain in abdomen for 3 months Symptom _____ Location _____ Duration _____

3 PRESENT ILLNESS Give a complete description of your illness

Date of first Symptoms ___/___/___
How did symptom(s) start _____
How did symptom(s) progress _____
What brings it on _____ What relieves it _____
What makes it worse _____ Associated symptoms _____

Recently, symptoms have been:
- ☐ More Frequent
- ☐ Less Frequent
- ☐ More Intense
- ☐ Less Intense
- ☐ Continuous
- ☐ Periodic

| MEDICATIONS | DOSAGE | FREQUENCY |
|---|---|---|
| | | |
| | | |
| | | |
| | | |
| | | |

If #2 above is pain, check the one(s) that best describe it.
- ☐ Severe  ☐ Burning  ☐ Sharp
- ☐ Moderate  ☐ Needle-like  ☐ Dull
- ☐ Mild  ☐ Stabbing  ☐ Gnawing
- ☐ Continuous  ☐ Cramping  ☐ Sudden
- ☐ Periodic  ☐ Deep  ☐ Gradual
- ☐ Intermittent  ☐ Superficial  ☐ Shifting

4 REVIEW OF SYSTEMS Check only the ones you NOW have or have had RECENTLY

GENERAL: Weakness, Fatigue, Fever, Chills, Night Sweats, Fainting

SKIN: Color Changes, Nail Changes, Hair Changes, Moles, Rashes, Itching, Sores, Dryness

HEAD: Headaches, Injuries, Bumps, Last Eye Exam ___/___/___

EYES: Blurred Vision, Glaucoma, Redness, Itching, Burning, Swelling, Pain, Dryness, Tearing, Glasses, Contacts, Cataracts

EARS: Hard of Hearing, Deafness, Ringing, Discharge, Earache, Itching, Loss of Balance, Dizziness, Room Spins

NOSE: Decreased Smell, Bleeding, Pain, Discharge, Obstruction, Post Nasal Drip, Deviated Septum, Runny Nose, Sinus Congestion

MOUTH: Bleeding Gums, Sores, Dental Problems, Pain, Bad Breath, Loss of Taste, Dry Mouth, Ulcers, Blisters

THROAT: Soreness, Bad Tonsils, Hoarseness, Pain, Trouble Swallowing, Recurrent Infections

NECK: Neck Enlargement, Stiff Neck, Soreness, Lumps, Masses

BREASTS: Discharge, Lumps, Pain, Bleeding, Nipple Changes, Skin Changes, Bloatedness

LUNGS: Cough, Phlegm, Blood, Short of Breath, Wheezing, Pain, Congestion, Inhalant Exposure

HEART: Murmur, Palpitations, Rapid Heartbeat, Swollen Extremities, Cold Extremities, Chest Pain/Pressure, Varicose Veins, Blood Clots, Blue Extremities

BLOOD: Anemia, Low Blood Iron, Easy Bruising, Easy Bleeding, Swollen Nodes, Painful Nodes, Sugar in Blood, Red Spots

GASTROINTESTINAL: Abdominal Pain, Nausea, Vomiting, Bloatedness, Belching, Heartburn, Indigestion, Irregular Bowel Habits, Constipation, Diarrhea, Gas, Hemorrhoids, Hernias, Poor Appetite, Food Intolerance, Bloody Stools, Black Stools

GENITOURINARY: Urgency, Incontinence, Straining, Back Pain, Frequent Voiding, Stones, Burning, Bed Wetting, Bloody Urine, Small Stream, Discharge, Sores, Impotence, Dribbling, Cloudy Urine, URINE COLOR: ___

GYNECOLOGICAL: Spotting Between Periods, Menstrual Cramps, Spotting After Menopause, Discharge, Itching, Painful Intercourse, Irregular Periods, Hot Flashes, Pain Between Periods
Contraception – Type _____
Age at first period _____
Age at menopause _____
Duration of cycle _____
Duration of flow _____
No. of pregnancies _____
No. of births _____
No. of miscarriages _____
No. of abortions _____

MENSTRUAL FLOW: ☐ Heavy ☐ Moderate ☐ Light
Last Period _____
Last Pap Smear _____
Last Mammogram _____

MUSCULOSKELETAL: Muscle Pain, Muscle Weakness, Muscle Cramps, Muscle Twitching, Joint Stiffness, Joint Pain, Joint Swelling, Joint Deformities, Injuries, Tenderness, Curvature of Spine, Back Pain, Hot Joints

NEUROLOGICAL: Seizures, Vertigo, Dizziness, Hand Trembling, Loss of Sensations, Incoordination, Loss of Facial Expressions, Weak Grip, Paralysis, Difficulty of Speech, Tingling, Loss of Memory, Numbness

PSYCHIATRIC: Hyperventilation, Insecurity, Depression, Troubled Sleep, Irritable, Anxiousness, Undecidedness, Timid, Hallucinations, Loss of Memory, Alcoholism, Drug Addiction, Drug Dependency, Suicidal Thoughts, Extreme Worry, Sexual Problems

ENDOCRINE: Weight Loss, Weight Gain, Hoarseness, Heat Intolerance, Cold Intolerance, Breast Changes, Hair Changes, Extreme Thirst, Voice Changes Appendix I (Page 1 of 2)

5 PAST MEDICAL HISTORY Check only the ones you have had in the PAST.

Past general state of health: ☐ Excellent ☐ Good ☐ Fair ☐ Poor

- ☐ Hay Fever
- ☐ Mumps
- ☐ Measles
- ☐ Rheumatic Fever
- ☐ Allergies
- ☐ Anemia
- ☐ Cancer
- ☐ Tumor
- ☐ Blood Disease
- ☐ Leukemia

- ☐ Skin Trouble
- ☐ Cataracts
- ☐ Tonsillitis
- ☐ Sinusitis
- ☐ Goiter
- ☐ Breast Trouble
- ☐ Asthma
- ☐ Bronchitis
- ☐ Pleurisy
- ☐ Pneumonia

- ☐ Tuberculosis
- ☐ Heart Trouble
- ☐ Varicose Veins
- ☐ Phlebitis
- ☐ Hypertension
- ☐ Stroke
- ☐ Ulcers
- ☐ Jaundice
- ☐ Gallstones
- ☐ Liver Trouble

- ☐ Hepatitis
- ☐ Parasites
- ☐ Dysentery
- ☐ Colitis
- ☐ Polyps
- ☐ Kidney Infections
- ☐ Kidney Stones
- ☐ Bladder Trouble
- ☐ Diabetes
- ☐ Syphilis

- ☐ Gonorrhea
- ☐ Hernia
- ☐ Sexual Problems
- ☐ Prostate Problems
- ☐ Hemorrhoids
- ☐ Arthritis
- ☐ Gout
- ☐ Migraines
- ☐ Epilepsy
- ☐ Paralysis

- ☐ Polio
- ☐ Mental Illness
- ☐ Alcoholism
- ☐ Depression
- ☐ Nervous Breakdown
- ☐ Others

| ILLNESSES · INJURIES · OPERATIONS | DATE | HOSPITAL | TREATMENT | PHYSICIAN |
|---|---|---|---|---|
| | | | | |
| | | | | |
| | | | | |
| | | | | |
| | | | | |
| | | | | |

| IMMUNIZATIONS/VACCINATIONS | BLOOD TYPE | BLOOD TRANSFUSIONS | LAST CHEST X-RAY | ALLERGIES |
|---|---|---|---|---|
| ☐ DPT ☐ Measles<br>☐ Mumps ☐ Pneumococcal<br>☐ Smallpox ☐ Influenza<br>☐ Typhoid ☐ Polio<br>☐ Tetanus ☐ MMR | ☐ A+ ☐ A−<br>☐ B+ ☐ B−<br>☐ AB+ ☐ AB−<br>☐ O+ ☐ O−<br>☐ Other ___ | No. of Transfusions ___<br>DATE(S) / REASONS<br>/ /<br>/ /<br>/ / | Date ___/___/___<br>☐ Normal ☐ Abnormal<br>LAST TB SKIN TEST<br>Date ___/___/___<br>☐ Positive ☐ Negative | |

6 FAMILY HISTORY List any of the diseases in Section 5 which run in your family.

| Blood Relatives Only | Age if Living | Age at Death | Cause of Death | State of Health | Illnesses |
|---|---|---|---|---|---|
| Father | | | | | |
| Mother | | | | | |
| Brother(s) | | | | | |
| Sister(s) | | | | | |
| Maternal Grandfather | | | | | |
| Maternal Grandmother | | | | | |
| Paternal Grandfather | | | | | |
| Paternal Grandmother | | | | | |

7 SOCIAL HISTORY Check the boxes and fill in.

Current Weight ___ Usual Weight ___ Maximum Weight ___ Minimum Weight ___

| MENTAL WORK | PHYSICAL WORK | EXERCISE | SMOKING | ALCOHOL |
|---|---|---|---|---|
| ☐ Heavy<br>☐ Moderate<br>☐ Light<br>No. of hours per day ___ | ☐ Heavy<br>☐ Moderate<br>☐ Light<br>No. of hours per day ___ | ☐ Heavy ☐ Moderate ☐ Light<br>Type(s) ___<br>No. of hours per week ___ | ☐ Current ☐ Previous<br>No. of packs per day ___<br>No. of years ___<br>Others ___ | ☐ Beer Amount/Week ___<br>☐ Liquor Amount/Week ___<br>☐ Wine Amount/Week ___<br>No. of years ___ |

| CAFFEINE | ASPIRINS | NUTRITION No. of portions per week | | | DRUGS No. of doses per week | | |
|---|---|---|---|---|---|---|---|
| (Coffee, Tea, Cola)<br>Cups per day ___<br>No. of years ___ | No. per day ___<br>No. of years ___<br>Others ___ | ___ Milk<br>___ Milk Products (Cheese, Butter)<br>___ Eggs<br>___ Vegetables | ___ Fruits<br>___ Breads<br>___ Cereal<br>___ Fish<br>___ Liver | ___ Beef<br>___ Pork<br>___ Chicken<br>___ Shellfish<br>___ Sweets | ___ Vitamins<br>___ Laxatives<br>___ Antacids<br>___ Diet Pills<br>___ Pain Pills | ___ Water Pills<br>___ Sleeping Pills<br>___ Nerve Pills<br>___ Potassium<br>___ Nutrasweet | ___ Saccharin<br>Others:<br>___<br>___<br>___ |

Date Reviewed ___/___/___ Reviewed By ___

PHYSICAL EXAMINATION Page 1

Admn. Date: _____  Admn. Time: _____
Admn. #: _____    Med.Surg □ Direct ER □

Vital Signs: BP ___/___  P ___  T ___°  R ___  HT. ___'___"  WT. ___  Race ___

---- GENERAL DESCRIPTION ----

□ WNL  □ ABNORMAL FINDINGS (Circle and give abnormality)   □ DEFERRED TO _____   □ OMIT SECTION
1. Development
2. Nourishment
3. State of Consciousness
4. Appearance, Attitude
5. Others

---- SKIN ----

□ WNL  □ ABNORMAL FINDINGS (Circle and give abnormality)   □ DEFERRED TO _____   □ OMIT SECTION
1. Texture
2. Color
3. Elasticity
4. Hair
5. Nails
6. Rashes, Sores
7. Others

---- LYMPH NODES ----

□ WNL  □ ABNORMAL FINDINGS (Circle and give abnormality)   □ DEFERRED TO _____   □ OMIT SECTION
1. Facial
2. Cervical
3. Supraclavicular
4. Epitrochlear
5. Axillary
6. Inguinal, Femoral
7. Others

---- EYES ----

□ WNL  □ ABNORMAL FINDINGS (Circle and give abnormality)   □ DEFERRED TO _____   □ OMIT SECTION
1. Lids, Conjunctivae, Lac. Glands
2. Sclera, Cornea, Ant. Chamber
3. Pupillary Reflexes
4. Fundus
5. EOM', Nystagmus, Visual Acuity
6. Others

---- EARS, NOSE, THROAT ----

□ WNL  □ ABNORMAL FINDINGS (Circle and give abnormality)   □ DEFERRED TO _____   □ OMIT SECTION
1. Ear Canals
2. Tympanic Membranes
3. Nasal Mucosa
4. Sinuses
5. Oral Mucosa, Saliv. Glands, Tongue
6. Tonsils, Pharynx, Gag Reflex
7. Others

---- HEAD AND NECK ----

□ WNL  □ ABNORMAL FINDINGS (Circle and give abnormality)   □ DEFERRED TO _____   □ OMIT SECTION
1. Head
2. Neck
3. Trachea
4. Thyroid
5. Jugulars, Carotids, Bruits
6. Others

---- BREASTS ----

□ WNL FEMALE: □ ABNORMAL FINDINGS (Circle and give abnormality)   □ DEFERRED TO _____   □ OMIT SECTION
1. Size, Position
2. Nipples
3. Skin, Masses, Nodules
4. Pain, Tenderness
5. Others □ WNL MALE: □ ABNORMAL FINDINGS (Circle and give abnormality)
1. Gynecomastia, Pain, Tenderness, Masses
2. Others

---- RESPIRATORY ----

□ WNL  □ ABNORMAL FINDINGS (Circle and give abnormality)   □ DEFERRED TO _____   □ OMIT SECTION
1. Bony Thorax
2. Expansion
3. Resp. Pattern, Rate
4. Percussion, Tactile Fremitus
5. Breath Sounds
6. Rales, Rhonchi, Wheezes, Rubs
7. Others Appendix II (Page 1 of 2)

CARDIOVASCULAR

[ ] WNL  [ ] ABNORMAL FINDINGS (Circle and give abnormality)  [ ] DEFERRED TO _____  [ ] OMIT SECTION
1. Precordium
2. Cardiac Size
3. Apex Beat, Thrills
4. Rhythm, Rate
5. Heart Sounds
6. Peripheral Pulses, Bruits
7. Murmurs, Gallops, Rubs, Clicks
8. Others

ABDOMEN

[ ] WNL  [ ] ABNORMAL FINDINGS (Circle and give abnormality)  [ ] DEFERRED TO _____  [ ] OMIT SECTION
1. Scars, Herniations, Distention
2. Rigidity, Pain, Guarding
3. Liver, Gallbladder
4. Spleen
5. Abd. Aorta
6. Kidneys
7. Masses
8. Shifting Dullness, Fluid Wave
9. Bowel Sounds
10. Others

GENITALIA

[ ] WNL FEMALE: [ ] ABNORMAL FINDINGS (Circle and give abnormality)  [ ] DEFERRED TO _____  [ ] OMIT SECTION
1. Ext. Genitalia
2. Vagina, Cervix, Dryness
3. Uterus, Ovaries, Tubes
4. Masses, Discharge
5. Others

[ ] WNL MALE: [ ] ABNORMAL FINDINGS (Circle and give abnormality)
1. Scrotum, Testes
2. Meatus, Penis
3. Hernias
4. Others

RECTUM

[ ] WNL  [ ] ABNORMAL FINDINGS (Circle and give abnormality)  [ ] DEFERRED TO _____  [ ] OMIT SECTION
1. Sphincter
2. Hemorrhoids
3. Prostate (Men Only)
4. Fissures, Fistulas, Masses, Tenderness
5. Others

BACK AND EXTREMITIES

[ ] WNL  [ ] ABNORMAL FINDINGS (Circle and give abnormality)  [ ] DEFERRED TO _____  [ ] OMIT SECTION
1. Spine
2. Extremities, ROM
3. Edema, Cyanosis, Varices, Ulcerations
4. Others

NEUROLOGICAL

[ ] WNL  [ ] ABNORMAL FINDINGS (Circle and give abnormality)  [ ] DEFERRED TO _____  [ ] OMIT SECTION
1. Mental Status
2. Cranial Nerves
3. Reflexes
4. Motor
5. Sensory
6. Others 1. EOM – Extraocular Movements   2. ROM – Range of Motion

DIAGNOSES

1. _____
2. _____
3. _____
4. _____
5. _____
6. _____
7. _____
8. _____
9. _____
10. _____

RECOMMENDATIONS

1. _____
2. _____
3. _____
4. _____
5. _____
6. _____
7. _____
8. _____
9. _____
10. _____

OFFICE RECORDS     DATE     PHYSICIAN'S SIGNATURE

```
Name:          Jane                  Admn. Date: 01/10
 DOB: 11/03/07                              Time: 12:00 AM
 Age: 81 yrs., 5 mos.                  DC Date: __/__/__
 Race: White                                Time: __:__ am/pm
 Sex: Female                          Admn. #:
 SS#: 221-06-3459                     Admn. Type: Medical - Direct
```

DISCHARGE PLANNING

Admitting Physician(s):          Harry

DIAGNOSES   (Check if DC Dx exactly same as admitting Dx; edit existing Dx; or add new DC Dx.)

1. Admission: CHEST PAINS R/O MI VS. UNSTABLE ANGINA
   Discharge: [ ]
2. Admission: HTN
   Discharge: [ ]
3. Admission: ACUTE EXACERBATION OF CHF
   Discharge: [ ]
4. Admission: HISTORY OF RHEUMATIC FEVER
   Discharge: [ ]
5. Admission: HISTORY OF HYPERTENSION
   Discharge: [ ]

Discharge Diagnoses:
6. _____
7. _____
8. _____
9. _____
10. _____

HOSPITAL COURSE

COMPLAINTS   (All unanswered complaints are omitted from narrative.)

S=stable, IS=improved spontaneously, RS=resolved spontaneously, IT=improved w/treatment, RT=resolved w/treatment

| | S | IS | RS | IT | | RT | | Other |
|---|---|---|---|---|---|---|---|---|
| C.C.: pain in/on chest........ | [ ] | [ ] | [ ] | [ ] | ____ | [ ] | ____ | [ ] ____ |
| General: weakness............. | [ ] | [ ] | [ ] | [ ] | ____ | [ ] | ____ | [ ] ____ |
| fatigue............. | [ ] | [ ] | [ ] | [ ] | ____ | [ ] | ____ | [ ] ____ |
| Skin: moles................... | [ ] | [ ] | [ ] | [ ] | ____ | [ ] | ____ | [ ] ____ |
| Eyes: blurred vision.......... | [ ] | [ ] | [ ] | [ ] | ____ | [ ] | ____ | [ ] ____ |
| Ears: loss of balance......... | [ ] | [ ] | [ ] | [ ] | ____ | [ ] | ____ | [ ] ____ |
| dizziness............. | [ ] | [ ] | [ ] | [ ] | ____ | [ ] | ____ | [ ] ____ |
| Nose: runny nose.............. | [ ] | [ ] | [ ] | [ ] | ____ | [ ] | ____ | [ ] ____ |
| Neck: stiff neck.............. | [ ] | [ ] | [ ] | [ ] | ____ | [ ] | ____ | [ ] ____ |
| Lungs: shortness of breath.... | [ ] | [ ] | [ ] | [ ] | ____ | [ ] | ____ | [ ] ____ |
| CV: palpitations............ | [ ] | [ ] | [ ] | [ ] | ____ | [ ] | ____ | [ ] ____ |
| swollen extremities..... | [ ] | [ ] | [ ] | [ ] | ____ | [ ] | ____ | [ ] ____ |
| chest pain or pressure.. | [ ] | [ ] | [ ] | [ ] | ____ | [ ] | ____ | [ ] ____ |
| GI: nausea................. | [ ] | [ ] | [ ] | [ ] | ____ | [ ] | ____ | [ ] ____ |

(Cont.)

Appendix III (Page 1 of 6)

DISCHARGE PLANNING

Name: Jane                                                                                 Page 2

HOSPITAL COURSE
COMPLAINTS (continued...)

S=stable, IS=improved spontaneously, RS=resolved spontaneously, IT=improved w/treatment, RT=resolved w/treatment

|  | S | IS | RS | IT | RT | Other |
|---|---|---|---|---|---|---|
| GU: polyuria | [ ] | [ ] | [ ] | [ ] | [ ] | [ ] |
| MS: muscle cramps | [ ] | [ ] | [ ] | [ ] | [ ] | [ ] |
| Neuro: dizziness | [ ] | [ ] | [ ] | [ ] | [ ] | [ ] |
| numbness | [ ] | [ ] | [ ] | [ ] | [ ] | [ ] |
| Psych: insomnia | [ ] | [ ] | [ ] | [ ] | [ ] | [ ] |

New Complaints:

|  | S | IS | RS | IT | RT | Other |
|---|---|---|---|---|---|---|
| .................. | [ ] | [ ] | [ ] | [ ] | [ ] | [ ] |
| .................. | [ ] | [ ] | [ ] | [ ] | [ ] | [ ] |
| .................. | [ ] | [ ] | [ ] | [ ] | [ ] | [ ] |
| .................. | [ ] | [ ] | [ ] | [ ] | [ ] | [ ] |
| .................. | [ ] | [ ] | [ ] | [ ] | [ ] | [ ] |
| .................. | [ ] | [ ] | [ ] | [ ] | [ ] | [ ] |
| .................. | [ ] | [ ] | [ ] | [ ] | [ ] | [ ] |
| .................. | [ ] | [ ] | [ ] | [ ] | [ ] | [ ] |

ABNORMAL PHYSICAL FINDINGS (All unanswered abnormal findings are omitted from narrative.)

S=stable, IS=improved spontaneously, RS=resolved spontaneously, IT=improved w/treatment, RT=resolved w/treatment

|  | S | IS | RS | IT | RT | Other |
|---|---|---|---|---|---|---|
| Head and Neck: | | | | | | |
| Jugulars; + JVD | [ ] | [ ] | [ ] | [ ] | [ ] | [ ] |
| Cardiovascular: | | | | | | |
| Heart Sounds; +S3 | [ ] | [ ] | [ ] | [ ] | [ ] | [ ] |
| Abdomen: | | | | | | |
| Liver; hepatomegaly | [ ] | [ ] | [ ] | [ ] | [ ] | [ ] |
| Back and Extremities: | | | | | | |
| Edema; + 3 pitting edema legs | [ ] | [ ] | [ ] | [ ] | [ ] | [ ] |

New Findings:

|  | S | IS | RS | IT | RT | Other |
|---|---|---|---|---|---|---|
| .................. | [ ] | [ ] | [ ] | [ ] | [ ] | [ ] |
| .................. | [ ] | [ ] | [ ] | [ ] | [ ] | [ ] |
| .................. | [ ] | [ ] | [ ] | [ ] | [ ] | [ ] |
| .................. | [ ] | [ ] | [ ] | [ ] | [ ] | [ ] |
| .................. | [ ] | [ ] | [ ] | [ ] | [ ] | [ ] |
| .................. | [ ] | [ ] | [ ] | [ ] | [ ] | [ ] |
| .................. | [ ] | [ ] | [ ] | [ ] | [ ] | [ ] |

VITAL SIGNS (List ONLY abnormal hosp. course V.S. List corresponding discharge V.S.)

|  | BP | P | T | R | Ht. | Wt. |
|---|---|---|---|---|---|---|
| Admission: | 162 / 94 | 88 | 98.4 | 24 | 5' 3" | 165 |
| Hosp. Course: | / |  |  |  |  |  |
| Discharge: | / |  |  |  |  |  |

DISCHARGE PLANNING

Name:    Jane                                                                                          Page 3

HOSPITAL COURSE (cont.)

LABS   (List ONLY abnormal labs and their corresponding discharge values. Leave blank if WNL.)

CHEMISTRY        [ ] Non-contributory (omit this section from narrative.)

|  | Glu | Na | K | Cl | CO2 | BUN | Cr | UrAc | Ca | Phos | TP | Alb | Glob |
|---|---|---|---|---|---|---|---|---|---|---|---|---|---|
| Admission: | | | | | | | | | | | | | |
| Hosp. Course: | | | | | | | | | | | | | |
| Discharge: | | | | | | | | | | | | | |

|  | Bili | Alk | LDH | SGOT | SGPT | Chl | Trig | Amy | Dig | T3 | T4 | FTI | TSH |
|---|---|---|---|---|---|---|---|---|---|---|---|---|---|
| Admission: | | | | | | | | | | | | | |
| Hosp. Course: | | | | | | | | | | | | | |
| Discharge: | | | | | | | | | | | | | |

Others: _____

HEMATOLOGY       [ ] Non-contributory (omit this section from narrative.)

|  | WBC | RBC | Hgb | Hct | MCV | PT | PTT | Plat | p | l | m | e | b |
|---|---|---|---|---|---|---|---|---|---|---|---|---|---|
| Admission: | | | | | | | | K | | | | | |
| Hosp. Course: | | | | | | | | K | | | | | |
| Discharge: | | | | | | | | K | | | | | |

(K=1000)

Others: _____

URINALYSIS       [ ] Non-contributory (omit this section from narrative.)

|  | Leuk (0-4) | Nitr (+/-) | Urob (0-3) | Prot (0-5) | PH (5-8.5) | Bld (0-5) | SpGr (1-1.03) | Keto (0-3) | Bili (0-3) | Glu (0-5) | Micro |
|---|---|---|---|---|---|---|---|---|---|---|---|
| Admission: | | | | | | | | | | | |
| Hosp. Course: | | | | | | | | | | | |
| Discharge: | | | | | | | | | | | |

Color: _____    Other: _____

Appendix III (Page 3 of 6)

DISCHARGE PLANNING

Name:          Jane                                                             Page 4

HOSPITAL COURSE (cont.)

DIAGNOSTIC STUDIES   (List ONLY abnormal studies and their corresponding discharge values. Leave blank if WNL.)

EKG       [ ] Non-Contributory (Omit this section from narrative.)

|              | WNL | Abnormality |
|---|---|---|
| Admission:   | [ ] | _____ |
| Hosp. Course:| [ ] | _____ |
| Discharge:   | [ ] | _____ |

CXR       [ ] Non-Contributory (Omit this section from narrative.)

|              | WNL | Abnormality |
|---|---|---|
| Admission:   | [ ] | _____ |
| Hosp. Course:| [ ] | _____ |
| Discharge:   | [ ] | _____ |

OTHER STUDIES   (Leave blank if NONE.)

| Exam | WNL | Abnormality |
|---|---|---|
| _____ | [ ] | _____ |
| _____ | [ ] | _____ |
| _____ | [ ] | _____ |
| _____ | [ ] | _____ |

CONSULTATIONS   (Leave blank if NONE.)

| Name | Specialty | Recommendations |
|---|---|---|
| _____ | _____ | _____ |
| _____ | _____ | _____ |
| _____ | _____ | _____ |
| _____ | _____ | _____ |

SURGICAL PROCEDURES / SURGERY   (Leave blank if NONE.)

| Physician | Procedure | Comments/Complications |
|---|---|---|
| _____ | _____ | _____ |
| _____ | _____ | _____ |
| _____ | _____ | _____ |

PROGNOSIS  [ ] Excellent   [ ] Good   [ ] Fair   [ ] Poor
           [ ] Deceased: Date __/__/__   Time __:__

Appendix III (Page 4 of 6)

DISCHARGE PLANNING

Name:        Jane                                                        Page 5

DISCHARGE INSTRUCTIONS

Diet:    (Check only if NOT on a regular diet)

[ ] 2gm Na              [ ] Low cholesterol     [ ] High fiber
    [ ] Clear liquid       [ ] Hypoglycemia diet   [ ] Puree diet
    [ ] Full liquid        [ ] Bland diet         [ ] Low triglyceride
    [ ] Low purine        [ ] Low residue
    [ ] ADA, _____ cal.   [ ] Reducing diet, _____ cal.
    Other: _____

Activity:    (Check only if ANY limitations)

[ ] Comp. bed rest    [ ] Ambulate indoors   [ ] Ambulate outdoors
    [ ] No bending        [ ] No lifting        [ ] No stretching
    [ ] No reaching
    Other: _____

Discharge Medications:

| Medications | Dosage | Frequency |
|---|---|---|
|  |  |  |
|  |  |  |
|  |  |  |
|  |  |  |
|  |  |  |
|  |  |  |
|  |  |  |

DISPOSITION    [ ] Home    [ ] Home w/home health    [ ] Nursing home
                  [ ] AMA     [ ] Rehabilitation inst.    [ ] Funeral home

| See: Physician | Phone | Date |
|---|---|---|
|  |  | __/__/__ |
|  |  | __/__/__ |
|  |  | __/__/__ |
|  |  | __/__/__ |

Special Instructions to Patient:

Physician's Comments:

DISCHARGE PLANNING

Name:   Jane

---
   /   /   _____
    Date           Physician's Signature

[ ] Copy of discharge summary to physician

---

What is claimed is:

1. A scheduling and reporting system for hospital patients comprising:
    means for entering data regarding the location of each patient, the location of each patient further being in the vicinity of one common area, said means for entering further includes entering data regarding physician orders for hospital services to be performed for each patient;
    means for scheduling the ordered services for each patient and for reporting the schedule information to said one common area;
    means for recording and reporting the results of the services administered to each patient to said common area; and
    means responsive to said recorded information for generating a discharge summary report for each patient at the conclusion of the hospitalization of such patient, said discharge summary including a summary of selective results of the services administered recorded;
    wherein said means for entering physicians orders for services includes entering priority data manifesting the priority of each ordered service; and
    wherein said means for scheduling includes means, responsive to said priority data for rescheduling previously scheduled services in response to higher priority data for subsequently entered services.

2. The invention according to claim 1 wherein said system further includes means for entering medical data regarding the progress of said patient during the hospitalization.

3. The invention according to claim 2 wherein said medical data includes nurses notes regarding the progress of each patient.

4. The invention according to claim 2 wherein said medical data includes physician notes regarding the progress of each patient.

5. The invention according to claim 4 wherein said medical data includes nurses notes regarding the progress of each patient.

6. The invention according to claim 2 wherein said means for generating said discharge summary report includes means for summarizing selective recorded results of said medical data entered.

7. The invention according to claim 6 wherein said medical data includes nurses notes regarding the progress of each patient.

8. The invention according to claim 1 wherein said means for reporting results provides such results in a form usable as a part of a patient's chart.

9. The invention according to claim 8 wherein said means for reporting results further includes printer means at each common area.

10. The invention according to claim 9 wherein each common area is a nurses station.

11. The invention according to claim 1 wherein said system includes a central computer system and said means for entering and means for reporting include terminals of said computer system.

12. The invention according to claim 1 wherein said system further includes storage means for storing data from which a chart for each patient may be reported.

13. The invention according to claim 1 wherein each common area is a nurses station.

14. A method of scheduling patient services and recording patient data for a hospitalized patient comprising the steps of:
    recording a location for each patient;
    recording physician orders for services to be performed upon each patient;
    automatically scheduling the services for each patient;
    recording the results of the performance of said services; and
    providing a discharge summary record for each patient;
    wherein the step of recording physician orders includes prioritizing the services ordered; and
    wherein said step of scheduling includes rescheduling in response to higher priorities for use of the services.

15. The method according to claim 14 wherein said method further includes the steps of recording patient data relating to the progress of each patient during the hospitalization and providing a documented copy of each record at a common area in the vicinity of the location of each for inclusion with each patient chart.

16. The method according to claim 15 wherein said discharge record includes a summary of selective recorded patient data relating to the progress of each patient during the hospitalization.

17. The method according to claim 14 wherein said discharge record includes a summary of selected recorded results.

18. The invention according to claim 14 wherein said method further includes the steps of selectively storing the information recorded to permit recreation of a patient chart for each patient.

* * * * *